United States Patent
Pratt et al.

(10) Patent No.: US 10,463,392 B2
(45) Date of Patent: Nov. 5, 2019

(54) FLUID-ASSISTED SKIN GRAFT HARVESTING

(71) Applicant: KCI Licensing, Inc., San Antonio, TX (US)

(72) Inventors: Benjamin A. Pratt, Poole Dorset (GB); Christopher Brian Locke, Bournemouth (GB); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 388 days.

(21) Appl. No.: 14/581,456

(22) Filed: Dec. 23, 2014

(65) Prior Publication Data
US 2015/0182241 A1 Jul. 2, 2015

Related U.S. Application Data

(60) Provisional application No. 61/922,399, filed on Dec. 31, 2013.

(51) Int. Cl.
*A61B 17/322* (2006.01)

(52) U.S. Cl.
CPC .... *A61B 17/322* (2013.01); *A61B 2017/3225* (2013.01)

(58) Field of Classification Search
CPC .......... A61B 17/322; A61B 2017/3225; A61B 2017/306; A61B 2017/308
See application file for complete search history.

(56) References Cited

U.S. PATENT DOCUMENTS

| | | | |
|---|---|---|---|
| 2,379,574 | A | 7/1945 | Goldthwait |
| 2,579,039 | A | 12/1951 | Evans |
| 2,721,555 | A | 10/1955 | Jenny |
| 3,054,404 | A | 9/1962 | Meek |
| 3,782,387 | A | 1/1974 | Falabella |
| 4,345,374 | A | 8/1982 | Jacobson |
| 4,600,533 | A | 7/1986 | Chu |
| 4,605,010 | A | 8/1986 | McEwen et al. |
| 4,666,447 | A | 5/1987 | Smith |
| 4,679,324 | A | 7/1987 | Krik |
| 4,773,418 | A | 9/1988 | Hettich |

(Continued)

FOREIGN PATENT DOCUMENTS

| | | |
|---|---|---|
| CN | 2125374 U | 12/1992 |
| CN | 2596950 Y | 1/2004 |

(Continued)

OTHER PUBLICATIONS

Office Action dated Dec. 18, 2014 for U.S. Appl. No. 13/120,799.
(Continued)

*Primary Examiner* — Todd J Scherbel
(74) *Attorney, Agent, or Firm* — Nelson Mullins Riley & Scarborough LLP; Thomas J. Engellenner; Reza M. Mollaaghababa (57) ABSTRACT

Methods, devices and systems are disclosed for generating and harvesting skin grafts having improved properties and for ensuring efficient and consistent blister formation and/or reducing patient harm and discomfort. In one aspect, the invention infuses a fluid into skin tissue at the donor site to enhance blister formation. The fluid infusion can occur before or after application of negative pressure—or can be cyclically applied before or after repeated applications of negative pressure.

29 Claims, 7 Drawing Sheets

(56) References Cited

U.S. PATENT DOCUMENTS

| | | | |
|---|---|---|---|
| 4,917,086 A | 4/1990 | Feltovich et al. |
| 5,015,584 A | 5/1991 | Brysk |
| 5,163,955 A | 11/1992 | Love et al. |
| 5,386,633 A | 2/1995 | Kanno |
| 5,433,221 A | 7/1995 | Adair |
| 5,441,490 A | 8/1995 | Svedman |
| 5,460,939 A | 10/1995 | Hansbrough |
| 5,476,478 A | 12/1995 | Jackson |
| 5,489,304 A | 2/1996 | Orgill |
| 5,496,339 A | 3/1996 | Koepnick |
| 5,545,222 A | 8/1996 | Bonutti |
| 5,571,098 A | 11/1996 | Domankevitz |
| 5,595,570 A | 1/1997 | Smith |
| 5,686,303 A | 11/1997 | Korman |
| 5,730,717 A | 3/1998 | Gelbfish |
| 5,759,193 A | 6/1998 | Burbank |
| 5,817,115 A | 10/1998 | Nigam |
| 5,888,219 A | 3/1999 | Bonutti |
| 5,914,261 A | 6/1999 | Boulton et al. |
| 5,914,264 A | 6/1999 | Korman |
| 5,921,980 A | 7/1999 | Kiru |
| 5,972,476 A | 10/1999 | Field |
| 5,976,163 A | 11/1999 | Nigam |
| 6,056,738 A | 5/2000 | Marchitto |
| 6,063,094 A | 5/2000 | Rosenberg |
| 6,071,247 A | 6/2000 | Kennedy |
| 6,071,267 A | 6/2000 | Zamierowski |
| 6,080,166 A | 6/2000 | McEwen et al. |
| 6,083,236 A | 7/2000 | Feingold |
| 6,248,114 B1 | 6/2001 | Ysebaert |
| 6,254,580 B1 | 7/2001 | Svedman |
| 6,358,260 B1 | 3/2002 | Ross |
| 6,364,908 B1 | 4/2002 | Ysebaert |
| 6,402,770 B1 | 6/2002 | Jessen |
| 6,436,078 B1 | 8/2002 | Svedman et al. |
| 6,585,939 B1 | 7/2003 | Dapprich |
| 6,612,310 B2 | 9/2003 | Sklar |
| 6,623,498 B1 | 9/2003 | Ziemer |
| 6,693,077 B1 | 2/2004 | Ruben et al. |
| 6,800,282 B1 | 10/2004 | Thomson |
| 6,860,904 B2 | 3/2005 | Bonutti |
| 7,056,327 B2 | 6/2006 | Levesque et al. |
| 7,078,582 B2 | 7/2006 | Stebbings |
| 7,137,979 B2 | 11/2006 | Conrad et al. |
| 7,207,998 B2 | 4/2007 | Feingold |
| 7,208,006 B2 | 4/2007 | Fleischman |
| 7,244,444 B2 | 7/2007 | Bates |
| 7,513,902 B2 | 4/2009 | Banbury et al. |
| 7,540,875 B2 | 6/2009 | Jessen |
| 7,625,384 B2 | 12/2009 | Eriksson |
| 7,651,507 B2 | 1/2010 | Mishra |
| 7,666,134 B2 | 2/2010 | Eriksson |
| 7,666,192 B2 | 2/2010 | Seegert |
| 7,708,746 B2 | 5/2010 | Eriksson |
| 7,727,760 B2 | 6/2010 | Guu et al. |
| 7,926,401 B2 | 4/2011 | Mishra |
| 8,002,779 B2 | 8/2011 | Barker et al. |
| 8,109,187 B2 | 2/2012 | Mishra |
| 8,162,957 B2 | 4/2012 | Mishra |
| 8,187,285 B2 | 5/2012 | Eriksson |
| 8,562,626 B2 | 10/2013 | Sabir |
| 8,617,181 B2 | 12/2013 | Sabir et al. |
| 8,926,631 B2 | 1/2015 | Sabir et al. |
| 9,173,674 B2 | 11/2015 | Sabir et al. |
| 2001/0029380 A1 | 10/2001 | Ysebaert |
| 2002/0052614 A1 | 5/2002 | GeBauer |
| 2002/0092529 A1 | 7/2002 | Rozier et al. |
| 2003/0009185 A1 | 1/2003 | Jessen |
| 2003/0069571 A1 | 4/2003 | Treat et al. |
| 2003/0152909 A1 | 8/2003 | Miranti |
| 2003/0212357 A1 | 11/2003 | Pace |
| 2004/0097967 A1 | 5/2004 | Ignon |
| 2004/0172045 A1 | 9/2004 | Eriksson |
| 2004/0186498 A1 | 9/2004 | Barnes et al. |
| 2004/0215217 A1 | 10/2004 | Banbury |
| 2004/0225309 A1 | 11/2004 | Eriksson |
| 2004/0230215 A1 | 11/2004 | Eriksson |
| 2004/0237744 A1 | 12/2004 | Lin |
| 2005/0038520 A1 | 2/2005 | Binette |
| 2005/0076921 A1 | 4/2005 | Rozier et al. |
| 2005/0101972 A1 | 5/2005 | Bhatavadekar |
| 2005/0221276 A1 | 10/2005 | Rozakis et al. |
| 2005/0234485 A1 | 10/2005 | Seegert |
| 2005/0244967 A1 | 11/2005 | Pearlman et al. |
| 2006/0079852 A1 | 4/2006 | Bubb et al. |
| 2006/0141616 A1 | 6/2006 | Guu |
| 2006/0173087 A1 | 8/2006 | Hyde et al. |
| 2006/0258956 A1 | 11/2006 | Haberstich et al. |
| 2006/0271070 A1 | 11/2006 | Eriksson |
| 2006/0287696 A1 | 12/2006 | Wright et al. |
| 2007/0183974 A1 | 8/2007 | Pearlman |
| 2007/0255168 A1 | 11/2007 | Hibner et al. |
| 2008/0146980 A1 | 6/2008 | Rousso et al. |
| 2009/0085286 A1 | 4/2009 | Grist et al. |
| 2009/0099122 A1 | 4/2009 | Klinman et al. |
| 2010/0012311 A1 | 1/2010 | Colongo |
| 2010/0042127 A1 | 2/2010 | Eriksson |
| 2010/0121311 A1 | 5/2010 | Seegert et al. |
| 2010/0145360 A1 | 6/2010 | Eriksson |
| 2010/0152651 A1 | 6/2010 | Boyden et al. |
| 2010/0152750 A1 | 6/2010 | Memar |
| 2010/0286635 A1 | 11/2010 | Watson, Jr. |
| 2010/0310823 A1 | 12/2010 | Albertelli et al. |
| 2011/0009882 A1 | 1/2011 | Remsburg et al. |
| 2011/0077664 A1 | 3/2011 | Schulz |
| 2011/0251602 A1 | 10/2011 | Anderson |
| 2011/0264115 A1 | 10/2011 | Asrani |
| 2011/0282309 A1 | 11/2011 | Adie et al. |
| 2012/0021186 A1 | 1/2012 | Schneider |
| 2012/0035599 A1 | 2/2012 | Sabir |
| 2012/0035618 A1 | 2/2012 | Sabir |
| 2012/0035619 A1 | 2/2012 | Sabir |
| 2012/0035620 A1 | 2/2012 | Sabir |
| 2012/0041430 A1 | 2/2012 | Anderson |
| 2012/0125798 A1 | 5/2012 | Baecker et al. |
| 2012/0136323 A1 | 5/2012 | Stasko et al. |
| 2012/0172894 A1 | 7/2012 | Sabir |
| 2012/0197267 A1 | 8/2012 | Sabir |
| 2012/0201755 A1 | 8/2012 | Rozakis et al. |
| 2012/0201793 A1 | 8/2012 | Bellomo |
| 2012/0244623 A1 | 9/2012 | Patel |
| 2012/0271320 A1 | 10/2012 | Hall |
| 2013/0041385 A1 | 2/2013 | Giovannoli |
| 2013/0145596 A1 | 6/2013 | Sabir et al. |
| 2013/0158627 A1 | 6/2013 | Gozani et al. |
| 2013/0204273 A1 | 8/2013 | Sabir et al. |
| 2014/0277454 A1 | 9/2014 | Locke et al. |
| 2015/0127077 A1 | 5/2015 | Ben Asher et al. |
| 2015/0182241 A1 | 7/2015 | Pratt et al. |

FOREIGN PATENT DOCUMENTS

| | | |
|---|---|---|
| CN | 101053528 A | 10/2007 |
| EP | 0099748 A1 | 2/1984 |
| EP | 1614404 A2 | 1/2006 |
| SU | 772544 A1 | 10/1980 |
| WO | 1992011879 A1 | 7/1992 |
| WO | 1995028886 A1 | 11/1995 |
| WO | 1996018432 A1 | 6/1996 |
| WO | 1996033768 A2 | 10/1996 |
| WO | 1997020509 A2 | 6/1997 |
| WO | 1998016158 A1 | 4/1998 |
| WO | 2003020333 A2 | 3/2003 |
| WO | 2003039382 A2 | 5/2003 |
| WO | 2003049626 A2 | 6/2003 |
| WO | 2003049783 A2 | 6/2003 |
| WO | 030068120 A1 | 8/2003 |
| WO | 03093418 A2 | 11/2003 |
| WO | 2004071313 A2 | 8/2004 |
| WO | 2004075764 A1 | 9/2004 |
| WO | 2004078032 A2 | 9/2004 |
| WO | 2004105576 A2 | 12/2004 |
| WO | 2005033273 A2 | 4/2005 |
| WO | 2005046428 A2 | 5/2005 |

(56) References Cited

FOREIGN PATENT DOCUMENTS

| WO | 2007034438 A2 | 3/2007 |
|---|---|---|
| WO | 2007117488 A2 | 10/2007 |
| WO | 2010014716 A1 | 2/2010 |
| WO | 2010036788 A2 | 4/2010 |
| WO | 2011038326 A2 | 3/2011 |
| WO | 2011059441 A1 | 5/2011 |
| WO | 2011075676 A2 | 6/2011 |
| WO | 2012019094 A2 | 2/2012 |
| WO | 2012019095 A2 | 2/2012 |
| WO | 2012019096 A1 | 2/2012 |
| WO | 2012019098 A1 | 2/2012 |
| WO | 2012102812 A1 | 8/2012 |
| WO | 2012145504 A1 | 10/2012 |
| WO | 20140152319 A2 | 9/2014 |

OTHER PUBLICATIONS

Awad, Chinese Cupping: A Simple Method to Obtain Epithelial Grafts for the Management of Resistant Localized Vitiligo, American Society of Dermatologic Surgery, Inc., Dermatol Surg, (2008), 34(9):1186-1193.
Balaji et al., Isolation of a Novel Population of Multipotent Stem Cells From Epidermal Layer of Human Skin, Biology and Medicine, (2010), 2(2):57-67.
Kreis et al., Expansion techniques for skin grafts: comparison between mesh and Meek Island (sandwich-) grafts, Burns, (1994), 20(1):S39-S42.
Lari et al., Expansion technique for skins grafts (Meek technique) in the treatment of severely burned patients, Burns, (2001), 27:61-66.
Meek et al., Successful Microdermagrafting Using the Meek-Wall Microdermatome, Am J Surg, (1958), 96(4):557-558.
Mulekar et al., Treatment of Vitiligo on Difficult-to-Treat Sites Using Autologous Noncultured Cellular Grafting, Dermatol Surg., (2009), 25(1):66-71.
International Search Report and Written Opinion dated Dec. 16, 2011 for PCT/US11/46737.
International Search Report and Written Opinion dated Dec. 23, 2011 for PCT/US11/46739.
International Search Report and Written Opinion dated Dec. 16, 2011 for PCT/US11/46738.
International Search Report and Written Opinion dated Dec. 6, 2011 for PCT/US11/46741.
European Examination Report dated Mar. 18, 2015 corresponding to European Application No. 11815368.3 (4 sheets.).
Office Action dated Feb. 20, 2015 with English Text of Office Action corresponding to Japanese Patent Application No. 2013-523359.
International Search Report dated Oct. 2, 2014 for PCT/US2014/027205.
International Search Report dated Mar. 13, 2015 for PCT/US2014/072180.
International Search Report dated Mar. 11, 2015 for PCT/US2014/072188.
PCT Notification of Transmittal of the International Search Report and the Written Opinion of the International Searching Authority, or the Declaration, PCT/US2014/072170, dated Mar. 19, 2015 (12 sheets).
[No Author Listed] BBC-GCSE Bitsize: Gore-tex, Article: http://www.bbc.co.uk/schools/gcsebitesize/science/ocr_gateway_pre_2011/carbon_chem/6_designer_polymers3.shtml; retrieved Apr. 22, 2015.
International Search Report and Written Opinion received in PCT/US2014/02737 dated Aug. 1, 2014; 12 pages.
International Search Report and Written Opinion received in PCT/US2012/068551 dated Feb. 15, 2013; 9 pages.
International Search Report and Written Opinion received in PCT/US2016/026918 dated Jun. 28, 2016; 10 pages.
International Search Report and Written Opinion received in PCT/US2016/060336 dated Feb. 10, 2017; 14 pages.
Invitation to Pay Additional Fees and Where Applicable, Protest Fee received in PCT/US2017/018431 dated May 26, 2017; 20 pages.
Sams et al., Useful adjuncts to harvest split-thickness skin grafts. Dermatol Surg. Dec. 2004; 30(12 Pt 2):159 1-2.
Weyandt et ai;., Split-skin grafting from the scalp; the hidden advantage. Dermatol Surg. Dec. 2009; 35(12): 1873-9.

FLUID-ASSISTED SKIN GRAFT HARVESTING

CROSS-REFERENCE TO RELATED APPLICATION

This application claims priority to U.S. Provisional Application No. 61/922,399, filed Dec. 31, 2013. Prior application is incorporated herein by reference in its entirety

FIELD OF THE INVENTION

The present invention relates generally to devices and methods for generating and harvesting skin grafts.

BACKGROUND

Skin is the largest organ of the human body, representing approximately 16% of a person's total body weight. Because it interfaces with the environment, skin has an important function in body defense, acting as an anatomical barrier from pathogens and other environmental substances. Skin also provides a semi-permeable barrier that prevents excessive fluid loss while ensuring that essential nutrients are not washed out of the body. Other functions of skin include insulation, temperature regulation, and sensation. Skin tissue may be subject to many forms of damage, including burns, trauma, disease, and depigmentation (e.g., vitiligo).

Skin grafts are often used to repair such skin damage. Skin grafting is a surgical procedure in which a section of skin is removed from one area of a person's body (autograft), removed from another human source (allograft), or removed from another animal (xenograft), and transplanted to a recipient site of a patient, such as a wound site. Typically it is preferable to use an autograft instead of an allograft or a xenograft to reduce complications, such as graft failure and rejection of the skin graft.

A problem encountered when using an autograft is that skin is taken from another area of a person's body to produce the graft, resulting in trauma and wound generation at the donor site. Generally, the size of the graft matches the size of the recipient site, and thus a large recipient site requires removal of a large section of skin from a donor site, leading to increased pain and discomfort and longer healing time. Additionally, as the size of the section of skin removed from the donor site increases, so does the possibility of infection.

Techniques have been developed for harvesting a large number of smaller grafts, e.g., so-called micrografts, to reduce the trauma at the donor site. By removing only a fraction of the skin at a donor site and leaving regions of healthy skin surrounding the excised regions, a large amount of skin for transplantation can be obtained with less discomfort. Micrograft harvesting can also reduce the healing time and risk of infection at the donor site.

However, micrografts are often difficult to obtain due to the tendency of small skin excisions to curl or fold over onto themselves or the surgical instrument (e.g., dermatome), making them unsuitable for use. This folding/curling tendency is particularly problematic the thinner the layer is that is being obtained, such as the epidermal layer. To some extent, suction blistering can reduce this problem by raising a plurality of skin blisters that can be more readily captured (e.g., by an adhesive substrate) and maintained in a planar orientation until transplanted. Suction blistering typically involves both a source of negative pressure and a heat source to warm the skin which facilitates blister formation. However, current suction blistering methods and devices can sometimes be time-consuming, typically requiring 30 minutes or more to form harvestable grafts.

SUMMARY

Various aspects of the present teachings provide methods and devices for generating and harvesting skin grafts having improved properties, for ensuring efficient and consistent blister formation, and/or for reducing patient harm and discomfort. In one aspect, the invention infuses a fluid into skin tissue at the donor site to enhance blister formation. For example, devices and methods in accordance with the present teachings can generate an osmotic gradient between the external surface of the skin (e.g., the fluid to be infused) and within the skin at the donor site such that there is a net movement of water molecules into the skin (e.g., across the skin membrane). The fluid infusion can occur before or after application of negative pressure—or can be cyclically applied before or after repeated applications of negative pressure.

In accordance with various aspects of the present teachings, certain embodiments relate to a method for preparing a skin graft comprising the steps of applying a blister cutting device to a donor site on a subject's skin and infusing fluid into skin tissue at the donor site. A vacuum can be applied to generate a negative pressure within the device to raise at least one blister at the donor site and the cutter device can be activated to cleave the blister.

In various aspects, the fluid infused into the skin tissue at the donor site can be configured to promote the formation of blisters and/or the engorgement of the skin tissue. By way of example, infusing fluid into skin tissue can comprise exposing epidermal skin tissue at the donor site to a warm fluid, e.g., a fluid can having a temperature between 20° C. and 40° C., between 25° C. and 35° C., or between 28° C. and 33° C. Additionally or alternatively, the epidermal skin tissue can be exposed to purified or deionized water. In some embodiments, for example, the fluid to which the skin is exposed can be water having an electrical conductivity less than 11 microsiemens/cm (e.g., less than about 5 microsiemens/cm). In various aspects, the fluid can have a lower osmotic pressure than interstitial fluid in the skin at the donor site. Optionally, the fluid can additionally comprise an anesthetic agent or an antibiotic agent.

In various embodiments, one or more fluid infusion steps can be performed in order to aid in the formation of the blisters. By way of example, the step of infusing fluid into skin tissue further can comprise exposing the epidermal skin tissue to the fluid for a time duration between about 1 minute and 30 minutes. For example, the epidermal skin tissue can be exposed to the fluid for a time duration between about 5 minutes and 10 minutes. As indicated above, one or more fluid infusion steps can be performed. For example, after draining away the fluid to which the epidermal skin tissue was exposed for a duration, negative pressure can be applied to the skin tissue and then additional fluid can be infused into the skin tissue. In some aspects, the fluid can again be removed and negative pressure can be re-applied.

In various embodiments, the method can further include steps of applying an adhesive substrate to the blister prior to cleavage and harvesting the skin graft by removal of the substrate from the cutting device following blister cleavage. For example, the substrate can include a water resistant adhesive. In some aspects, the method can also include drying the donor site prior to applying the substrate.

The cutting device for use in methods in accordance with the present teachings can have a variety of configurations.

By way of example, the cutting device can include at least one fixed plate and at least one movable cutter plate, each plate having a plurality of holes through which suction blisters can be raised when the holes of the fixed and movable plates are aligned. In such a device, cleaving the blisters can comprise moving the cutter plate to disrupt alignment of the holes and thereby separate the blisters from remaining skin at the donor site.

In accordance with various aspects of the present teachings, certain embodiments relate to a method for preparing a skin graft with a device comprising a device body, a sealing member, at least one fixed plate and at least one movable cutter plate, each plate comprising a plurality of holes and wherein as assembled the holes in the plates are aligned within the body. In various aspects, the method can comprise the steps of connecting the device to a donor site on a subject's skin and joining the sealing member and body together to define a sealed chamber. A warm hypotonic solution can then be delivered to the chamber such that skin exposed to the chamber (e.g., skin in fluid communication with the chamber via the aligned plate holes) can assimilate the fluid. Unassimilated fluid can be removed from the chamber and negative pressure can be applied to the chamber to pull the skin into the chamber through the holes and thereby raise a plurality of blisters. The chamber can then be unsealed and an adhesive substrate applied to the exposed blisters. To cut the blisters, the movable cutter plate can be actuated to disrupt the alignment of holes such that the substrate can be removed with the cleaved skin blisters. In some aspects, the method can also include transferring skin grafts to a subject by applying the substrate together with the cleaved skin blisters to a recipient site.

In one embodiment of the invention, a two part device for harvesting of skin microblisters is disclosed. The two parts are a harvester that is adapted for attachment to a target region of skin and head which delivers the infusion fluid and negative pressure to at least portions of the skin engaged by the harvester.

More specifically, the head is adapted for coupling to a cutting body ('harvester') that is disposable on a patient's skin and further adapted for coupling to the fluid and vacuum sources, the head further providing a sealing surface to engage with a mating surface on the cutting body such that, when the head is engaged with the cutting body on a patient's skin, a evacuated chamber is formed over a target region of skin; and, preferably, a heating element for raising the temperature of the target region of skin and, further preferably at least one viewing window for observing blisters formed by heating the skin in the evacuated chamber. The head can further include at least one light source, such as a light emitting diode (LED) for illuminating skin blisters as they are being raised.

Optionally, in addition to defining at least a portion of a fluid-receiving chamber, the head can further include a heating element (e.g., a resistive electrical heating element). The head can also include at least one temperature measuring element, such as a thermistor, for measuring the temperature of the skin or evacuated chamber.

The harvester is configured for placement on a target region of a patient's skin and further adapted to form a sealing engagement with the head and define the chamber for fluid infusion and application of negative pressure. In one embodiment, the harvester further includes at least one alignment plate having a plurality of holes through which skin blisters can be raised in the presence of negative pressure, and a cutting plate having at least one cutting surface for cleaving skin blisters after they are formed within the chamber.

In another preferred embodiment, the harvester includes a top alignment plate and a bottom alignment plate, with the cutting plate disposed therebetween. The top and bottom alignment plates can be joined together by a plurality of vertical posts that pass through slots in the cutting plate to maintain the fixed position of the top and bottom plates relative to each other, while permitting movement of cutting plate. The top plate, bottom plate, and cutting plate can each have a plurality of holes that are adapted to be concentrically aligned to facilitate blister formation. In certain embodiments, the holes of the top plate are larger than the holes of the bottom plate.

The cutting plate can includes a plurality of holes suitable for concentric alignment with holes in the alignment plate in a first position to facilitate blister formation and a plurality of cutting surfaces suitable for cleaving blister in a second position.

The harvester can further include an actuator for moving the cutting plate from the first position to the second position and the actuator can configured to also at least partially retract the cutting plate following blister cleavage.

In accordance with various aspects of the present teachings, certain embodiments relate to a system for raising and cutting a skin blister, the system comprising a harvester configured for placement on a target region of a patient's skin, the harvester defining a sealed chamber in fluid communication with the target region when the harvester forms a sealing engagement with the patient's skin. The harvester also includes at least one alignment plate having a plurality of holes through which skin blisters can be raised in the presence of negative pressure and a cutting plate having at least one cutting surface for cleaving skin blisters after they are formed within the chamber. The system can also include a reservoir containing a fluid to be infused into the patient's skin, a conduit fluidly coupling the reservoir to the chamber, and a pump for delivering the fluid from the reservoir to the chamber through the conduit. In some aspects, the harvester can include a coupler for coupling to the fluid conduit. In various aspects, the system can also include a reduced pressure source and a fluid flow pathway between the sealed chamber and the reduced pressure source, wherein the reduced pressure source is configured to generate negative pressure in said chamber.

The pump can comprise any pump mechanism known in the art and modified in accordance with the present teachings. By way of example, the pump can be a peristaltic pump. In some aspects, the pump can be a reversible pump configured to also remove fluid from the chamber following a dwell time. In related aspects, the reversible pump can be configured to deliver the fluid removed from the chamber to a waste reservoir. For example, the conduit can include a valve that can be actuated to divert flow through the conduit to the waste reservoir.

In some embodiments, the system can include a second pump for removing fluid from the chamber. The second can be configured to operate at a higher volumetric flow rate relative to the pump for delivering the fluid from the reservoir to the chamber so as to maintain a negative pressure within the chamber.

In various aspects, the system can also include a fluid heater associated with the reservoir for warming the fluid to be infused. By way of example, the fluid heater can be configured to warm the fluid to be infused to a temperature between 20° C. and 40° C., between 25° C. and 35° C., or between 28° C. and 33° C.

In some embodiments, the system can also comprise a controller for controlling operation of at least one of the pump, the fluid heater, and the valve. For example, the controller can be configured to control the pump so as to provide a predetermined dwell time of the fluid within the chamber, to activate the fluid heater so as to warm the fluid to a predetermined temperature, and/or to switch the valve so as to divert fluid flowing through the conduit to a waste reservoir when the pump is operating in a reverse mode.

In various aspects, the fluid can be selected from the group comprising purified water, deionized water, water having an electrical conductivity less than 11 microsiemens/ cm, and fluid having a lower osmotic pressure than interstitial fluid in the skin at the donor site.

These and other aspects of the devices of the invention are described in the figures, description and claims that follow. While various features have been individually described, such features are not mutually exclusive of each other. Any combination of design features disclosed herein can be used integrated into the devices of the invention.

DETAILED DESCRIPTION

In the following detailed description of non-limiting, illustrative embodiments, reference is made to the accompanying drawings that form a part hereof. Other embodiments may be utilized and logical, structural, mechanical, electrical, and chemical changes may be made without departing from the scope of this specification. To avoid detail not necessary to enable those skilled in the art to practice the embodiments described herein, the description may omit certain information known to those skilled in the art. The following detailed description is not to be taken in a limiting sense, with the scope of the illustrative embodiments being defined by the appended claims.

The term "micrograft" as used herein is intended to encompass skin grafts that have a width or length less than a millimeter, more preferably, less than 100 microns. A micrograft is an excised skin segment having at least one dimension parallel to the skin surface that is less than a millimeter, preferably less than 100 micrometers, more preferably in some applications less than 10 micrometers. The minimum width or length is preferably less than 500 micrometers, preferably less than 100 micrometers or less than 50 micrometers or less than 10 micrometers or less than 1 micrometer. For example, a micrograft can be generally circular, oval or oblong in a plane parallel to the skin surface and have a diameter or major axis that ranges from about 1 millimeter to 0.01 micrometers, or from about 100 micrometers to about 0.1 micrometers, or more preferably from about 50 to 1 micrometers. Micrografts also typically have a depth dimension that extends at least through the epidermis and preferably in some applications encompasses at least one layer of basal cells. The depth can range from about 500 micrometers to about 0.1 micrometers, preferably from about 100 micrometers to about 1 micrometer.

The term "harvesting" as used herein is intended to encompass the removal of one or more skin grafts from an skin graft generating device, such as, for example, a suction blister micrograft generator, as well as the transplantation of such skin grafts and any intermediate steps, such as culturing, expanding, stretching, treating or otherwise preparing a skin graft for transfer to a recipient site.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by 1/10 of the stated values, e.g., ±10%. For instance, a concentration value of about 30% can mean a concentration between 27% and 33%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

The present invention generally relates to devices and systems that are adapted to infuse a fluid into skin at a donor site to enhance the formation of one or more blisters (e.g., suction blisters) and cut the raised blister(s). In various aspects, fluid infusion can be effective to soften and/or swell the skin with fluid. For example, in some aspects, infusing fluid comprises generating an osmotic gradient between the external surface of the skin (e.g., the fluid to be infused) and within the skin at the donor site such that there is a net movement of water molecules into the skin (e.g., across the skin membrane).

Blister raising devices (e.g., a skin graft harvester) in accordance with the present teachings can define a chamber than can be sealed in fluid communication with the skin of the patient so that a fluid can be instilled into and removed from the chamber, and so that negative pressure can be applied to raise the blister(s), for example, following fluid infusion. A cutting member integrated within the harvester can then be actuated following one or more cycles of fluid infusion and application of negative pressure to harvest the skin grafts (e.g., micrografts) formed thereby.

Figure 1:
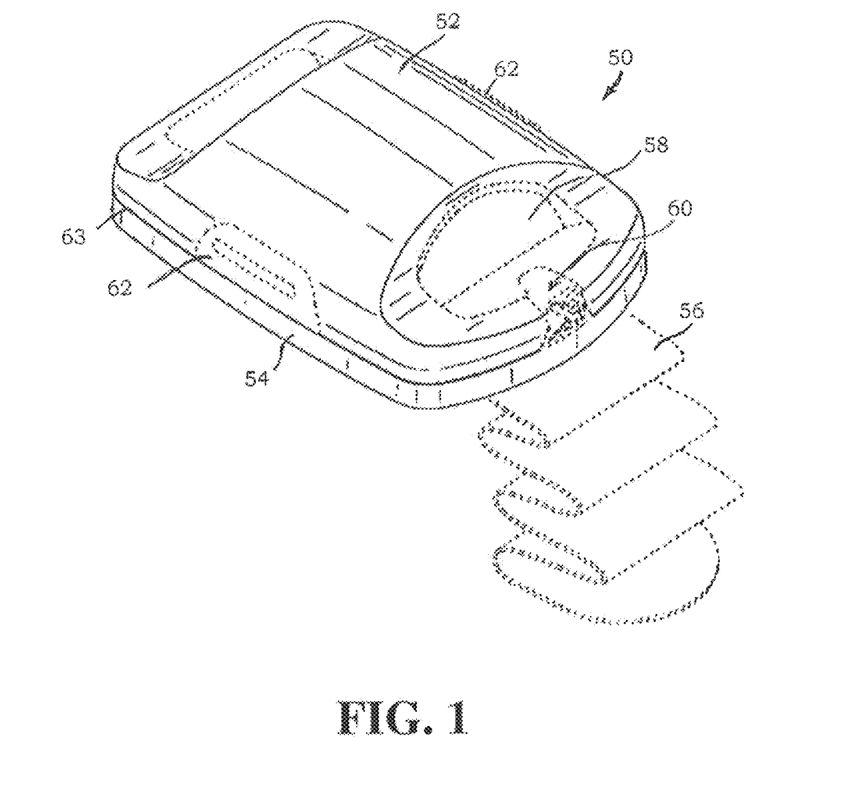
FIG. 1 is a schematic perspective of a skin blister harvesting device according to the invention.

In certain embodiments, skin graft harvesters in accord with the present teachings can include a head portion that can be removably coupled to a harvester body positioned at the donor site of a subject's skin. Together, the head portion and the body portion can define the sealed chamber enabling fluid infusion into the skin and application of negative pressure to the skin. For example, with reference now to FIGS. 1-4, an exemplary skin graft harvester 50 for infusing a fluid into skin at the donor site is depicted. As shown in FIG. 1, the harvester 50 includes a detachable head portion 52 and a harvester body 54, which contains a blister cutting assembly 76 (see FIG. 3). The harvester body 54 is adapted for placement on a patient's skin at a donor site where skin grafts are to be obtained (e.g., on the inner thigh), and secured in place so as to form a seal against the skin surface, for example, with strap 56 (shown in phantom). The head portion 52 also includes a sealing surface or seal 63 such that when the head 52 and body 54 are joined together and the harvester 50 is coupled to a fluid source or vacuum pump via coupler 60, for example, a sealed chamber is defined for infusing fluid into the patient's skin and/or for applying a reduced pressure the patient's skin through an array of holes 78 in the cutting assembly 76 (see FIG. 3). By way of example, the sealed chamber can contain an infusion fluid that generates an osmotic gradient across the skin membrane such that there is a net movement of water molecules into the skin.

The coupler 60 can have a variety of configurations but generally couples the internal chamber to an external fluid source or source of negative pressure via one or more conduits. Although shown and described as part of the head portion 52, it should be clear that the coupler 60 for fluid delivery and/or evacuation of the chamber can be part of either the head 52 or the body 54 and that the fluid to be infused and negative pressure can be applied separately via multiple couplings or via a single conduit. With specific reference now to FIGS. 2A and 2B, an exemplary conduit 42 is depicted as being coupled to the coupler 60, the exemplary conduit 42 comprising a flexible polymer tube having one or more internal lumens for providing fluid communication between the chamber and one or both of a fluid source (e.g., an infusion fluid reservoir, as discussed in detail below) or a reduced-pressure source (not shown). The conduit 42 can be fluidly coupled to the coupler 60 in any suitable manner, such as, for example, using any one of known fluid-tight couplings (e.g., by an adhesive, solvent or non-solvent bonding, welding, mechanical interlock, interference fit, etc.). The distal end (not shown) of the conduit 42 can also include any one of known couplings for attachment to the fluid source or reduced-pressure source. As discussed otherwise herein, after attachment of the head 52 to the body 54, a fluid source and/or vacuum source can be attached to the conduit 42 to deliver to and/or remove fluid from the chamber of the harvester 50 and/or generate negative pressure therein.

The reduced-pressure source can be effective to seal the harvester 50 to the skin surface and/or evacuate the chamber to aid in the formation of suction blisters. It will be appreciated that the reduced pressure source can be any suitable device for providing reduced pressure, such as, for example, a vacuum pump, wall suction, or other source. Although the terms "vacuum" and "negative pressure" may also be used to describe the pressure applied to the tissue site, the actual pressure applied to the tissue site may be more than the pressure normally associated with a complete vacuum. As used herein, "reduced pressure" generally refers to a pressure less than the ambient pressure at a tissue site being subjected to treatment. Typically, this reduced pressure will be less than the atmospheric pressure. The reduced pressure may also be less than a hydrostatic pressure at a tissue site. Consistent with the use herein, an increase in reduced pressure or vacuum pressure typically refers to a relative reduction in absolute pressure. Thus, an increase in reduced pressure corresponds to a reduction in pressure (more negative relative to ambient pressure) and a decrease in reduced pressure corresponds to an increase in pressure (less negative relative to ambient pressure). Unless otherwise indicated, values of pressure stated herein are gauge pressures. While the amount and nature of reduced pressure applied to a tissue site will typically vary according to the application, the reduced pressure will typically be between −5 mmHg and −500 mmHg, and more typically in a therapeutic range between −100 mmHg and −200 mmHg. It will also be appreciated that the reduced pressure delivered may be constant or varied (e.g., patterned or random) and may be delivered continuously or intermittently. For example, as discussed in detail below, it may be particularly beneficial to alternate fluid infusion steps and the application of reduced pressure in the formation of blisters.

Additional details on reduced pressure sources can be found, for example, in U.S. patent application Ser. No. 11/646,918 filed Dec. 28, 2006; U.S. patent application Ser. No. 11/810,027 filed Jun. 4, 2007; U.S. patent application Ser. No. 12/661,293 filed Mar. 15, 2010; and U.S. patent application Ser. No. 13/052,873 filed Mar. 21, 2011. The disclosures of each of these patent applications are incorporated by reference in their entireties.

In various aspects, the head portion 52 or harvester body 54 can also include one or more additional features to facilitate the harvesting of skin grafts in accordance with the present teachings. By way of example, the exemplary head portion 52 can include inter alia coupling elements for securely engaging the head portion 52 to the harvester body 54, a blister raising mechanism (e.g., via application of reduced pressure, heat, or both), and one or more windows for observation of skin blisters being formed within the chamber.

Figure 2A:
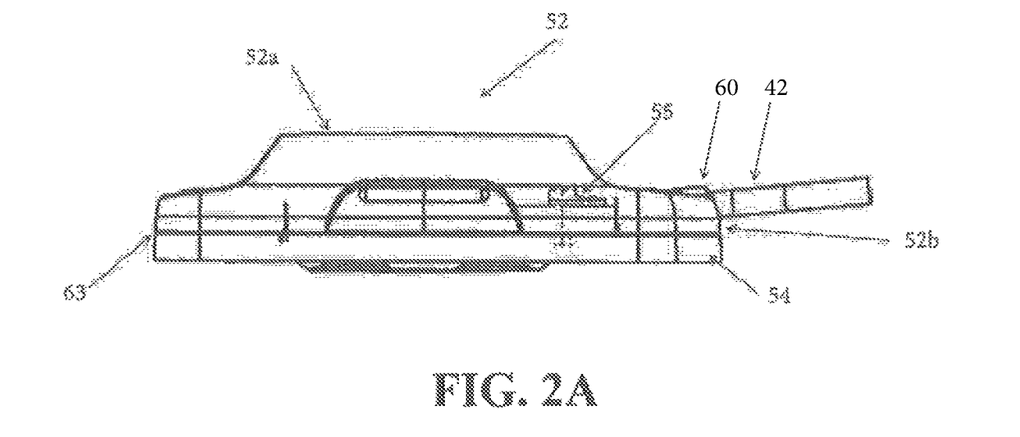
FIG. 2A is a schematic plan view of a removable head portion of a skin blister harvesting device according to the invention.
Figure 2B:
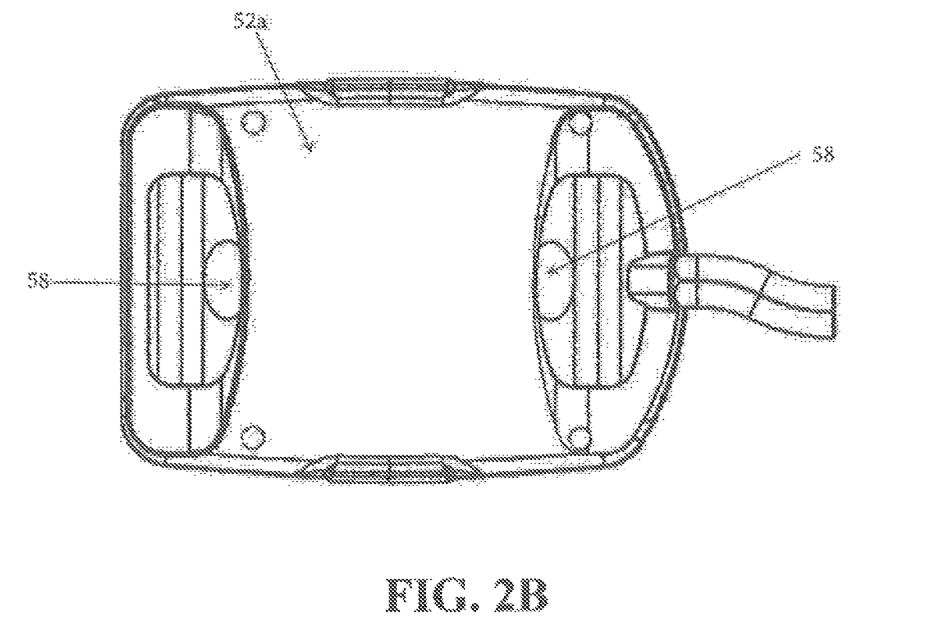
FIG. 2B is a schematic top view of a removable head portion of a skin blister harvesting device shown in FIG. 2A.

As shown in FIGS. 2A and 2B, the exemplary head portion 52 includes a topmost, proximal portion 52a and a distal portion 52b that is configured to securely engage to the harvester body 54 so as to define a sealed chamber between the head portion 52 and the harvester body 54. The distal portion 52b can itself define a sealing surface configured to form a seal with the harvester body 54, or additionally or alternatively, a sealing member 63 can be disposed between the head portion 52 and the harvester body 54 to provide a fluid seal such that the chamber can be filled with fluid and/or evacuated by the reduced pressure source with limited leakage.

As will be appreciated by a person skilled in the art, a sealing member 63 can be formed from any material that allows for a fluid seal adequate to prevent fluid from leaking from the chamber between the head portion 52 and body portion 54 and to maintain reduced pressure within the chamber in view of the particular reduced pressure source or system involved. The sealing member 63 can comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom having, for example, an MVTR (inverted cup technique) of 14400 g/m$^2$/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber;

polyurethane (PU); EVA film; co-polyester; silicones; a silicone drape; a 3M Tegaderm® drape; a polyurethane (PU) drape such as one available from Avery Dennison Corporation of Pasadena, Calif.; polyether block polyamide copolymer (PEBAX), for example, from Arkema, France; or other appropriate material.

It will also be appreciated by a person skilled in the art that the detachable mating of the head portion 52 and harvester body 54 can be accomplished in a variety of ways. By way of example, the head 52 can include one or more holes 53 for mating with a corresponding mating feature of the harvester body 54. The holes 53, which can extend through the head portion 52, can receive pins (not shown) extending proximally from an upper surface of the harvester body 54. Alternatively, for example, after aligning the head portion 52 with the harvester body 54, a screw can be inserted distally through the holes 53 to threadingly engage corresponding threaded bores formed in the harvesting body 54 to ensure secure engagement of the head 52 and body 54. Additionally, in some aspects, the head portion can include one or more release levers 62 that enable the seal to be broken, for example, after the source of reduced pressure has been deactivated, such that the head 52 can be disengaged (e.g., lifted off) the harvester body 54.

As shown in FIG. 2A, the head portion 52 can additionally include a heating component 55 for warming the skin so as to aid in the formation of suction blisters. The heating component 55, which can be by way of non-limiting example a light source (e.g., an array of incandescent lamps) or a resistive heating element (e.g., a nichrome wire) disposed within the head portion 52, can be powered via a coupler 60 to a power source in a base unit (not shown). The heat generated by the heating component 55 can be controlled, for example, by cycling the heating component 55 as needed to maintain a desired temperature within the chamber. In some aspects, the heating component 55 can be capable of emitting heat ranging between about 100° C. to about 750° C. (e.g., about 500° C.).

In some embodiments, for example, for those in which the heating component 55 comprises a light source that emits electromagnetic radiation, the distal portion 52b of the head 52 can include a transparent or a translucent surface that seals off the heating component 55 from fluid within the chamber and/or facilitates the transmission of electromagnetic radiation emitted from the heating element 55 within head 50 to the cutting mechanism disposed within the body 54, and subsequently heat to the patient's skin.

In certain aspects, the transparent or translucent surface can be made of material that allows light having a wavelength between about 10 nanometers to about 3000 nanometers to be transmitted through the surface. Suitable materials for transmission of light include, for example, crystalline materials such as sapphire, quartz, silicon, garnet, sillenite, fused silica, fused quartz, titanium dioxide, zinc selenide, calcium fluoride, barium fluoride, zinc sulphide, caesium iodide, germanium, thallium bromo-iodide, lithium fluoride, magnesium fluoride, potassium bromide, sodium chloride, or strontium fluoride. Other suitable materials include glass such as silica glass, fluoride glass, aluminosilicate glass, phosphate glass, borate glass, chalcogenide glass, or polymer glass. Optionally, the crystalline material or glass can be polarized. In certain aspects, the distal portion 52b of the head 52 includes two transparent or translucent surfaces in a stacked configuration with an airspace therebetween. The airspace between the transparent or translucent surfaces can have a variety of dimensions, for example, between about 0.1 mm to about 25.0 mm. The two transparent or translucent surfaces can be the same materials, or different materials. For example, the two surfaces can both be made of a glass or crystalline material. Alternatively, one of the surfaces can be a glass material, while the other surface is a crystalline material.

With reference now to FIG. 2B, the head portion 52 can optionally include one or more windows 58 for observation of skin blisters being formed within the chamber (e.g., by application of reduced pressure, heat, or both). It will be appreciated that the viewing windows 58 can be located to provide optimal viewing of blister formation within the hollow body of the device. As shown in FIG. 2B, a plurality of viewing windows 58 are integrated within the head 52 to allow for alternative views of blister formation, or allow more than one user to monitor the development of the blisters. The viewing window 58 can be made of any transparent material. In preferred embodiments, the viewing window 58 is comprised of optical quality material, for example an optical polymer, an optical glass, or an optical crystal. Such materials can further include one or more of an anti-fogging material, an anti-scratch coating, or an anti-glare coating, located on either the or both the interior surface, the exterior surface, or both. In certain embodiments, the viewing window can be made of a heat resistant material to prevent warping or distortion from the heating component 55 within the head 50.

In some aspects, at least a portion of the viewing window(s) 58 can include a magnification lens to facilitate viewing of the blisters during formation. Additionally or alternatively, the viewing window(s) 58 can include one or more calibration marks etched or painted on the viewing window(s) 58 for monitoring blister formation. Where the viewing window(s) 58 include a magnification lens, the calibration marks can be calibrated to the magnification power of the lens to approximate the actual dimensions of the forming blister, such as the actual height, the actual diameter, or both. When the desired blister size is formed as gauged by the calibration marks, the blisters can be cut, as otherwise described herein.

Figure 3:
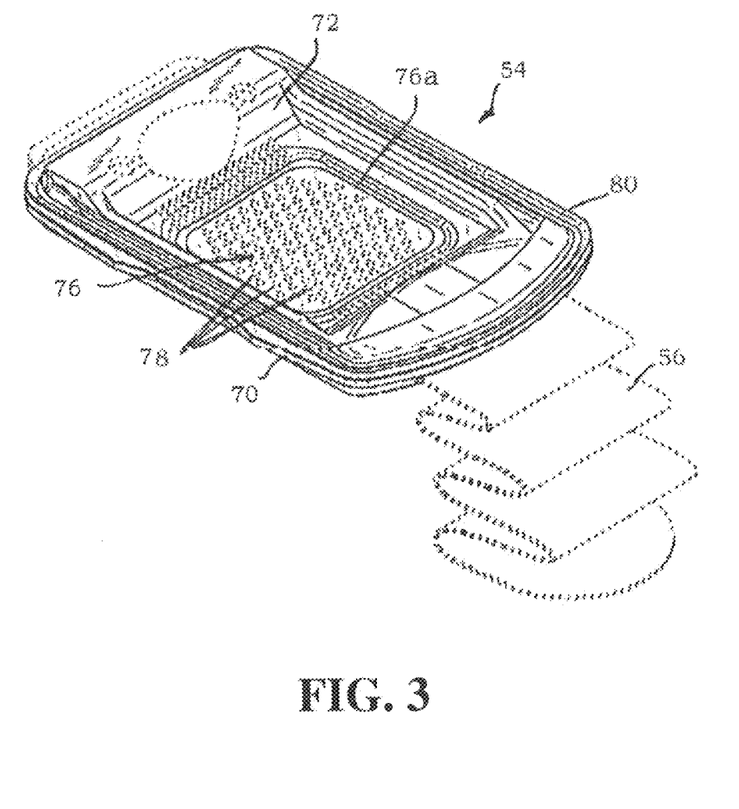
FIG. 3 is a schematic perspective of a base portion of skin blister harvesting device according to the invention.

With reference now to FIG. 3, the exemplary harvester body 54 of the skin graft harvester 50 of FIG. 1 with the head portion 52 removed and the cutting assembly 76 exposed is depicted. The harvester body 54 can include a base portion 70, a sled 72, and actuator handle 80. The cutting assembly 76 includes a plurality of plates, each having a plurality of holes 78 that can be initially aligned and through which skin blisters can be drawn by heat and/or application of suction when the head 52 is joined to the harvester body 54 and the reduced pressure source is activated. Once the blisters are formed, they can be cleaved by the cutting assembly 76. As will be discussed in detail with reference to FIG. 4, by actuation (e.g., pulling up) of handle 80, the sled 72 can be caused to move horizontally such that one of the plates below the top plate 76a moves relative to the top plate 76a (because of its linkage to the sled 72), thereby occluding the alignment of holes 78 and cleaving the raised blisters from the donor's skin.

Figure 4:
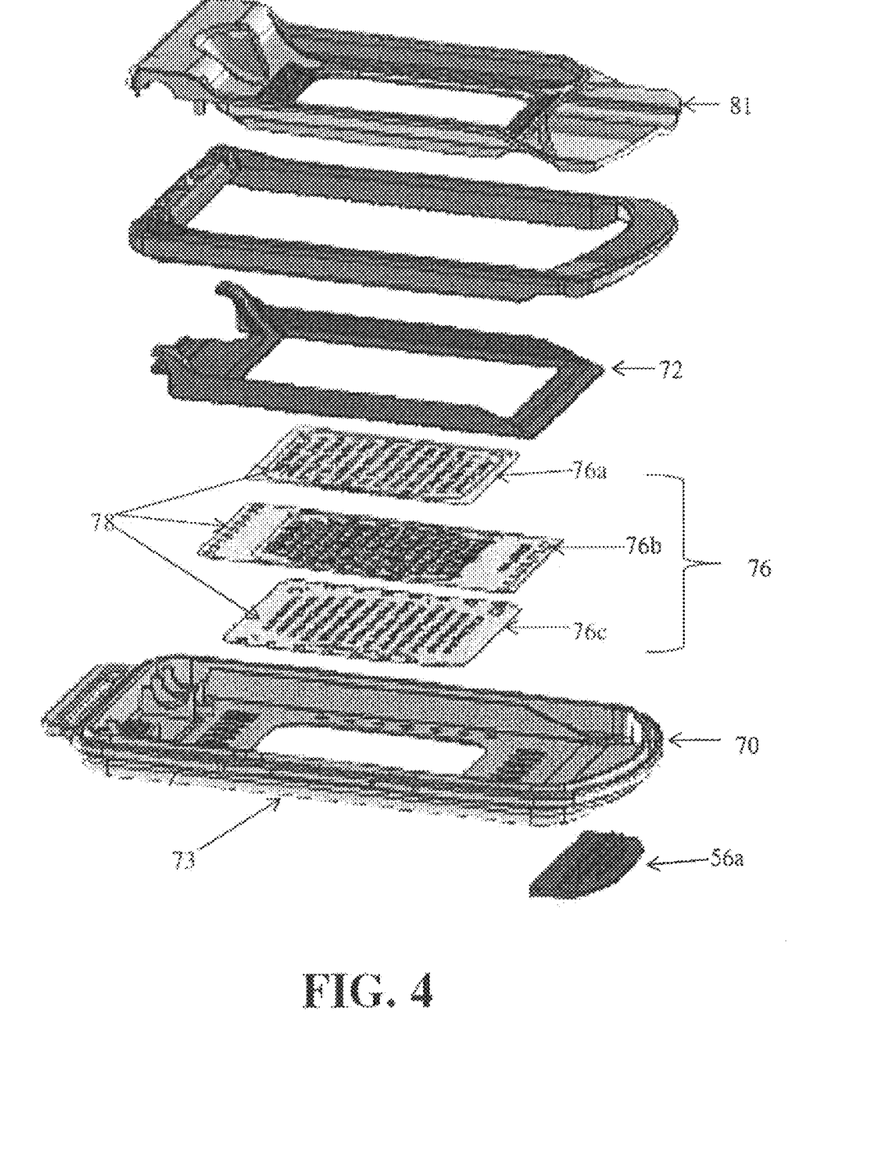
FIG. 4 is a schematic exploded view of the harvester base portion shown in FIG. 3.

FIG. 4 is an exploded view of the harvester body 54 of FIG. 3. As shown in FIG. 4, the exemplary harvester body 54 includes a base portion 70 within which the cutting assembly 76 and actuator assembly can be disposed and a top element 81. The distal surface of the base portion 70 also includes a sealing member 73 that surrounds the donor site when the harvester 50 is coupled to the patient's skin. The sealing member 73 can be formed from any material that allows for a fluid seal adequate to prevent fluid from leaking from the chamber between the patient's skin and the harvester 50 and/or to prevent leakage of gas into the reduced pressure chamber. The sealing member 73 can comprise, for example, a flexible, biocompatible material. By way of example, the sealing member one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom having, for example, an MVTR (inverted cup technique) of 14400 g/m$^2$/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, Calif.; polyether block polyamide copolymer (PEBAX), for example, from Arkema, France; or other appropriate material such as a low Shore polymer ring. Optionally, the base portion 70 can include a strap coupler 56a to facilitate attachment of the harvester body 54 to a patient's skin (e.g., for joining a strap 56 as depicted in FIG. 3 around a patient's leg for harvesting skin from the inner thigh).

With reference again to FIG. 4, in the depicted exemplary embodiment, the cutting assembly 76 comprises a top and a bottom guide plate 76a,c and a middle cutter plate 76b disposed therebetween, each plate 76a-c having a plurality of holes 78 which can initially be concentrically aligned and through which blisters can be raised. For example, when the plates 76a-c are aligned and negative pressure is applied to the chamber, blisters can be formed and protrude through the aligned holes 78 in all three plates. The cutter plate 76b, each hole 78 of which can include a cutting edge, can be coupled to the sled 72 so as to move in a direction parallel to guide plates 76a,c in a one-time, back and forth motion upon actuation of the handle 80. Alternatively, in certain embodiments, the plates 76a-c can be coupled in their stacked configuration via one or more elastic members (e.g., springs), which serves to keep the plates 76a-c in alignment until a lateral force is applied to one of the plates. Upon removal of the force, the elastic members can return the plates 76a-c to their original positions (e.g., can retract the middle cutter plate 76b) such that the arrays of holes 78 in each plate 76a-c are once again in concentric alignment.

The size of the holes 78 in each plate 76a-c can depend on the size of the graft needed, with larger holes being used in each plate to produce larger grafts. In certain embodiments, the holes 78 range between 1 mm and 12 mm in diameter, or any specific value in between. In certain embodiments, the holes 78 in the array can vary in size and/or shape between the bottom plate 76c, middle plate 76b and/or top plate 76a. For example, the holes 78 of the top plate 76a can be larger than those of the bottom plate 76b to facilitate blister formation and/or growth of the blister.

It will be appreciated that the various features of the cutting plate can be formed, for example, lithographically by depositing a resist and patterning it (e.g., by expose to light) such that portions of an initial plate blank are protected from etching while other portion can be removed by etching (e.g., to form the holes and alignment slots). The resist can also be patterned to provide a limited amount of protection to the cutting edge portions, thereby shaping them to have less thickness (e.g., like a knife edge). The sharpness of the cutting edges can be further enhanced by electro-polishing which will reduce the overall thickness of the cutting plate.

As indicated above, the exemplary harvester body 54 also includes a cutter drive sled 72 and handle 80 for controlling the movement of the cutter plate 76b. By way of example, the cutter plate 76b is coupled to the sled 72 in a configuration that translates the rotational movement of the handle 80 into lateral movement of the cutter plate 76b. For example, the handle 80 can be linked to the sled 72 via a generally cylindrical bar (axle) that rotates about an axis when the handle 80 is lifted up or closed. In some aspects, the axle can include two non-symmetric protrusions. During rotation of the handle 80, and thus the axle, the protrusions can engage with corresponding protrusions formed on the sled 72 so as to cause the lateral movement of the sled 72 and the cutter plate 76b that is coupled thereto, thereby cutting the blisters that protrude through the holes 78.

Additional details on harvesters useful in connection with the present invention can be found in U.S. patent application Ser. No. 13/839,518 filed Mar. 15, 2013; U.S. patent application Ser. No. 13/346,329 filed Jan. 9, 2012; U.S. patent application Ser. No. 13/436,318 also filed Jan. 9, 2012; U.S. patent application Ser. No. 13/014,737 filed Jan. 27, 2011; U.S. patent application Ser. No. 12/851,656 filed Aug. 6, 2010; U.S. patent application Ser. No. 12/851,621 filed Aug. 6, 2010; U.S. patent application Ser. No. 12/851,703 filed Aug. 6, 2010; and U.S. patent application Ser. No. 12/851,682 filed Aug. 6, 2010. The contents of each of the above-referenced related applications are herein incorporated by reference in their entireties.

Figure 5:
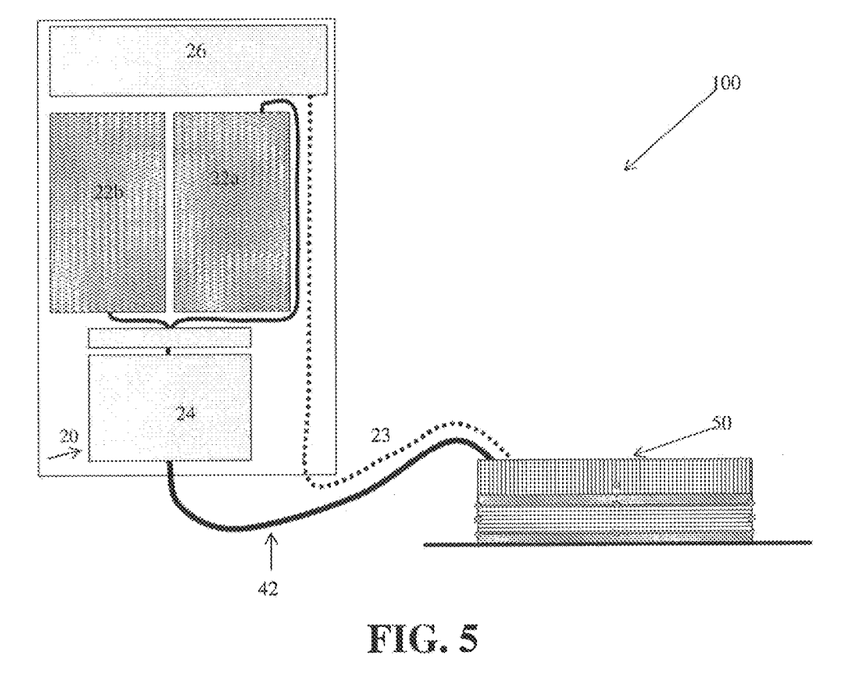
FIG. 5 is a schematic block diagram of a fluid infusing system for skin blister formation according to the invention.
Figure 6A:
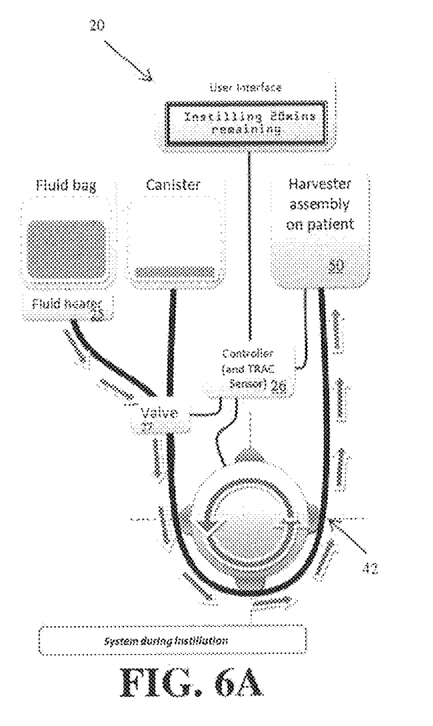
FIG. 6A is a schematic illustration of the operation of the system of FIG. 5 during fluid instillation.
Figure 6B:
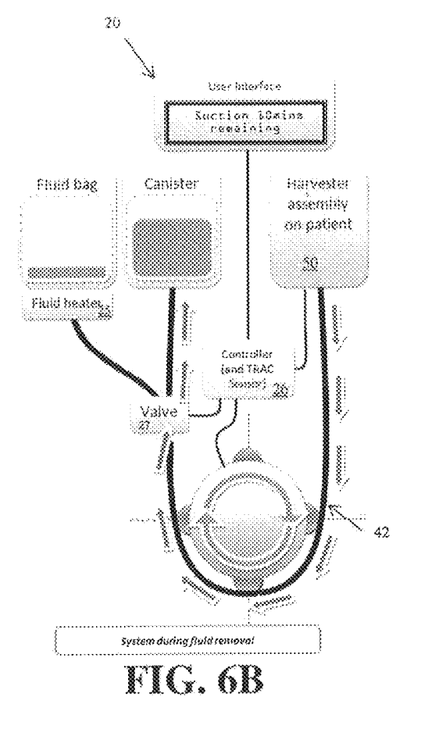
FIG. 6B is a schematic illustration of the operation of the system of FIG. 5 during fluid removal.

With reference now to FIGS. 5 and 6, an exemplary system 100 incorporating the skin graft harvester 50 of FIGS. 1-4 and a fluid infusion system 20 will now be described. As indicated above, the skin graft harvester 50 defines a sealed chamber for containing the fluid to be infused in the patient's skin when the skin graft harvester 50 is secured to the patient's skin so as to substantially form a seal against the skin surface (e.g., via compression and/or negative pressure within the chamber). As shown in FIG. 5, the exemplary fluid infusion system 20 includes a fluid reservoir 22a in fluid communication (e.g., via conduit 42 and coupler 60 of FIG. 1) with the sealed chamber of the skin graft harvester 50 and one or more pumps 24 for delivering and/or removing fluid from the sealed chamber. Optionally, as will be discussed in detail below, the fluid infusion system 20 can additionally include a controller 26 (e.g., a TRAC controller with a user interface) for controlling the heating, delivery, and/or removal of the fluid from the sealed chamber and for allowing the user to select various parameters of the fluid infusion step (e.g., dwell time). In related aspects, a fluid control line 23 can couple the chamber of the harvester 50 to the controller 26 such that the controller 26 can monitor the performance of the system 100 (e.g., detect blockages in the conduit 42) and/or control the pressure and temperature of the fluid or gas within the chamber.

In accordance with the present teachings, the fluid reservoir 22a can contain the fluid to be infused into the patient skin through the holes 78 in the cutting assembly 76. In a preferred embodiment, the fluid is configured to promote the local engorgement of the skin tissue and/or the formation of blisters when the fluid is disposed within the chamber of the harvester 50 (e.g., by softening the skin). For example, the fluid to be infused is selected such that the fluid (or a portion thereof) preferentially moves (e.g., diffuses) across the skin barrier. It will be appreciated in light of the present teachings that the fluid to be infused can have a variety of properties for promoting the net movement of fluid into the skin, including having a reduced concentration of solutes relative to the skin tissue. For example, in some aspects, the fluid can be purified or deionized water so as to promote diffusion of water from areas of high concentration (i.e., the fluid within the chamber) to areas of low concentration (i.e., the patient's skin). By way of example, the fluid to which the skin is exposed can be water having an ionic concentration such that the electrical conductivity is less than 11 microsiemens/cm (e.g., less than about 5 microsiemens/cm). Additionally or alternatively, fluids within the chamber can have a lower osmotic pressure than the interstitial fluid in the skin at the donor site such that fluid from the chamber is preferentially absorbed into the patient's skin. Moreover, in some aspects, one or more additives can be added to the fluid to be infused so as to reduce the patient's discomfort and/or prevent infection at the donor site during and/or after the blisters are harvested. By way of example, the fluid to be infused can additionally comprise an anesthetic agent (e.g., Benzocaine), an antibiotic agent (e.g., Bactine), and/or additional skin softeners.

As shown in FIGS. 6A and 6B, the fluid infusion system 20 can additionally include a heater 25 to warm the fluid to be infused into the skin prior to delivery to the chamber of the skin graft harvester 50. Like the identity of the fluid, the temperature of the fluid can also have an effect on the engorgement of the skin at the donor site, as well as on the blister formation itself. For example, by exposing the patient's skin to a warmed fluid (e.g., a fluid can having a temperature between 20° C. and 40° C., between 25° C. and 35° C., or between 28° C. and 33° C.), it is pores in the skin tissue can be opened such that the fluid is more quickly incorporated into the skin tissue, thereby reducing the duration of the infusion and/or blister raising procedure. Moreover, in some aspects, the fluid can be sufficiently warmed such that the harvester 50 need not include a heating component 55, as described above with reference to FIG. 2A.

With reference again to FIG. 5, the fluid infusion system 20 also includes a pump 24 for delivering the fluid from the fluid reservoir 22a through the conduit 42 to the sealed chamber of the harvester 50. The pump 24 can generally comprise any pump mechanism known in the art and modified in accordance with the present teachings. By way of example, the pump 24 can comprise any of a peristaltic, reciprocating, rotary, gear, plunger, piston, and diaphragm pump, and gravity, impulse and centrifugal pumps, all by way of non-limiting example. It will further be appreciated that one or more additional pumps (hereinafter a "second pump") can be utilized in the fluid infusion system 20 to remove fluid from the chamber of the harvester 50 (e.g., after the skin has been exposed for a specified or sufficient duration or "dwell time"). The second pump can return the fluid to the fluid reservoir 22a (i.e., recycled in a closed circuit) or deliver the waste fluid (i.e., fluid to which the skin has been exposed) to a designated waste reservoir 22b. It will further be appreciated that the second pump can be the same or different from the pump 24 and can be selected to operate with the same or different parameters as the pump 24. By way of example, the second pump can be operated at a higher volumetric flow rate than the pump 24 such that a reduced pressure is maintained in the chamber of the harvester 50 during the fluid infusion step(s), thereby helping to seal the harvester 50 to the patient's and/or aiding the formation of suction blisters.

In some aspects, the pump 24 can instead be a bi-directional pump that can be used to both deliver the fluid to be infused to the chamber of the harvester 50, as shown in FIG. 6A, and remove fluid therefrom (e.g., after the skin has been exposed for a specified or sufficient duration), as shown in FIG. 6B. For example, the bi-directional pump can be intermittently reversed such that the fluid to which the skin is exposed can be changed to provide fresh and/or newly warmed fluid during the fluid infusion step(s). Moreover, as discussed above, rather than returning the spent or waste fluid to the fluid reservoir 22a, the fluid infusion system 20 can instead include a waste reservoir 22b for receiving and/or storing the waste fluid. By way of example, the conduit 42 can include a valve 27 such that waste fluid can be diverted to the waste reservoir 22b when the bi-directional pump is operated to remove fluid from the chamber of the harvester 50.

Certain embodiments of device 50 integrate consumable/single-use and re-usable, sterilizable or cleaned components, thereby providing a reliable system that is easy to maintain. All components of device 50 that come into contact with the donor and/or recipient tissue (both single-use and reusable components) must be sterile/sterilized to reduce the risk of infection. In some aspects, the polymeric conduit 42 and other non-single use polymeric portions of the fluid infusion system 20 can be manufactured with an anti-microbial material within the polymer to as to prevent the growth of bacteria therein.

Figure 7:
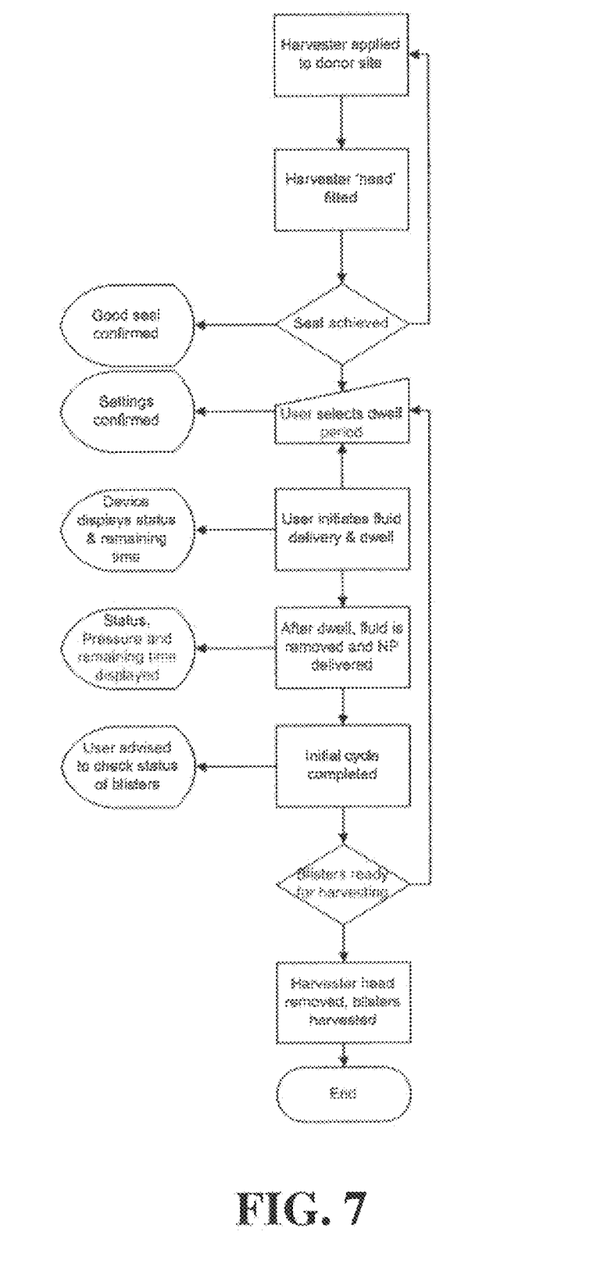
FIG. 7 is a flow diagram illustrating one method for skin blister formation according to the invention.

With reference to FIG. 7, an exemplary method 700 for utilizing the system 100 for generating and harvesting skin grafts will now be described. As indicated above, the fluid infusion system 20 can include a controller 26 (e.g., a TRAC controller with a user interface) for controlling the heating, delivery, and/or removal of the fluid from the sealed chamber. Though the use of the fluid infusion system 20 is described with reference to FIG. 7 as a series of steps that can be implemented with the controller 26, it will be appreciated that the methods for raising and harvesting skin grafts in accordance with the present teachings can be performed manually (e.g., a user can select the dwell time and initiate reversal of a pump for removal of fluid from the chamber of the harvester 50).

As shown in step 710, the process 700 for producing and harvesting a plurality of skin grafts can begin by applying the harvester body 54 to a desired donor site (e.g., an inner thigh of a patient). The strap 56 can be applied to ensure adequate compression of the sealing member 73 against the patient's skin. After the harvester body 54 is securely engaged to the patient, the harvester head 52 can be coupled to the body 54, for example, through coupling of one or more mating features (e.g., holes 53 in the head 52 for receiving pins of the body 54), as indicated in step 720.

At this point, it can be determined whether a sealed chamber is formed within the skin graft harvester 50. Specifically, it can be determined whether the sealing member 63 forms a seal between the harvester body 54 and head 52 and further, whether the harvester body 54 is sealed to the patient's skin via sealing member 73. By way of example, in step 730, the controller can activate the reduced pressure source to apply a reduced pressure within the chamber of the harvester 50. If the harvester 50 is sealed to the skin and the harvester body 54 to the harvester head 52, no leaks should be detected (e.g., a substantially constant pressure is maintained within the chamber).

After confirming that a seal has been achieved, the user can be prompted to input the parameters for the fluid to be infused into the patient's skin, for example, using a user interface associated with the controller 26, as shown in step 740. As will be appreciated in light of the present teachings, the user can select any number of parameters for delivery and/or removal of the fluid to be infused including the dwell time (e.g., in a range between about 1 minute and about 30 minutes, between about 5 to about 10 minutes, about 5 minutes), the temperature of the fluid, and the input and output fluid flow rate, all by way of non-limiting example. Upon confirming the settings, the controller can activate the fluid delivery system 20 to deliver the fluid to the sealed chamber via the conduit 42, as shown in step 750. By way of example, the controller 26 can activate the fluid heater 25 and pump 24 to operate according to the desired settings. As discussed above, during the fluid infusion step 750, the fluid (or a portion thereof) within the chamber can be intermittently exchanged for fresh and/or warmed fluid. Moreover, during this fluid infusion step 750, the skin in fluid communication with the fluid within the chamber via the one or more aligned holes 78 in the cutting assembly 76 will absorb or uptake the fluid (or portions thereof). The skin will swell slightly as the fluid is absorbed by the skin and the dermis engorges. It is noted that during the step 750, the user interface can display the status of the dwell (e.g., temperature of the fluid, chamber pressure, remaining dwell time).

Once the skin has become sufficiently exposed to the fluid within the chamber of the harvester 50, or alternatively, after the pre-determined dwell time, the controller can cause the fluid to be removed to the waste reservoir 22b through reversing the pump 24 (or activating a second pump), as indicated by step 760. Additionally, the negative pressure source can be activated (or increased) such that the reduced pressure in the chamber is increased to promote the formation of suction blisters through the aligned holes 78 in the cutting assembly 76. By way of example, the pressure in the chamber can be reduced to a pressure in the range of from about −125 mmHg to about −400 mmHg. Without being bound by a particular theory, it is believed that the generation of such pressures stimulate the engorged skin tissue to express the absorbed fluids in an effort to re-balance the osmotic pressure, thereby causing the skin to protrude through the aligned holes 78 in the cutting assembly 76 and form blisters. Optionally, the heating element 55 in the head portion 52 can also be activated to promote the formation of blisters. It is noted that during the step 760, the user interface can display the status of the application of the negative pressure (e.g., the pressure itself and remaining time). As will be appreciated in light of the current teachings, the amount of negative pressure applied, the amount of time the vacuum is maintained, and/or the depth of the holes 78 in plates 76a-c (i.e., the plate thickness) can determine what type of graft will be harvested, (e.g., epidermal graft, split thickness graft, or full thickness graft).

As indicated above, the harvester 50 can include one or more viewing windows 58 that enable the user to monitor the progress of blister formation. Accordingly, the user can choose to end the blister formation step 760 once the blisters have been sufficiently formed, or alternatively, as shown in step 770, the controller 26 can prompt the user to check the status of the blisters after a pre-determined duration of the application of reduced pressure. The produced blisters may be fluid-filled or may not contain any fluid, i.e., a blister having air within. The skin and blister area is generally not damaged and patient discomfort is minimal. If the blisters are sufficiently formed, the user can initiate the blister harvesting step 780 as discussed in detail below. If on the other hand the number and/or size of the blisters is not yet sufficient, the controller 26 can re-initiate one or more additional cycles of fluid infusion and suction, as indicated in FIG. 7. It will be appreciated in light of the current teachings that the cycle of fluid infusion and suction can be further optimized for the formation of blisters. By way of example, shorter, but repeated cycles of fluid infusion and application of negative pressure may be more effective in the formation of blisters relative to fewer, longer dwell times and suction steps.

Once the blisters are satisfactorily formed, the user can initiate the blister harvesting step 780 by deactivating the negative pressure source and removing the head 52 from the harvester body 54. By way of example, the release levers 62 can be actuated to unseal the head 52 from the body 54 such that the head 52 can be lifted therefrom. As will be appreciated by a person skilled in the art, a substrate for capturing the blisters can optionally be applied to the surface of the top plate 76a such that the substrate is in direct contact with the raised blisters. In some aspects, the surface of the blisters can be dried prior to coupling the substrate thereto. To cut the raised blisters, handle 80 is actuated such that the middle, cutter plate 76b is moved relative to the top and bottom plates 76a,c, thereby interfering with the alignment of the holes 78 and causing the cutting surface defined by one or more holes 78 in the cutter plate 76b to cut the raised blisters. As the raised blisters are cut, they can be simultaneously transferred/retained on the substrate in substantially the same configuration as the array of holes 78, thereby resulting in a substrate containing a plurality of uniformly spaced and oriented micrografts.

The substrate can have a variety of configurations, but in certain embodiments, includes an adhesive on one side that facilitates attachment of the blisters thereto the substrate. The substrate material may have intrinsic adhesive properties, or alternatively, a side of the substrate may be treated with an adhesive material, e.g., an adhesive spray such as LEUKOSPRAY (Beiersdoerf GmbH, Germany). The substrate can be, for example, a deformable non-resilient material that may be manipulated, e.g., stretched or expanded, from a first configuration to a second configuration, and once in the second configuration, there is no residual stress on the substrate such that the substrate can be stretched to an expanded configuration without returning to its original size. In some aspects, a soft polyurethane or polyethylene can be used as the substrate. Other materials suitable for use with the system 100 include low density polyethylene, linear low density polyethylene, polyester copolymers, polyamide copolymers, and certain silicones. In one embodiment, the substrate can be Tegaderm™.

Ultimately, the substrate containing the plurality of uniformly spaced and oriented (i.e., substantially planar) micrografts can be applied to a recipient of site of a patient. The size of the area at the recipient site can be about the same size as the area of the substrate having micrografts adhered thereto. This size generally will be greater than the area of the original graft tissue that was removed from the donor site to form the micrografts. Prior to applying the grafts to the recipient site, the site can be prepared to receive the grafts using any technique known in the art. Necrotic, fibrotic or avascular tissue should be removed. The technique used to prepare the site will depend, for example, on damage to the recipient site. For example, epidermal tissue, if present at the recipient site, can be removed to prepare the area for receiving the micrografts. Burned or ulcerated sites may not need removal of epidermal tissue, although some cleaning of the site or other preparation of the site may be performed. Wounds should be debrided and then allowed to granulate for several days prior to applying the graft. Most of the granulation tissue should be removed since it has a tendency to harbor bacteria. Applying silver sulfadiazine to the wound for 10 days prior to grafting reduces the bacterial count greatly.

The substrate having the plurality of blister grafts can be placed over the area to be treated to form a dressing. A portion of the substrate having the grafts can be positioned over the area to be repaired, e.g., the area from which the epidermal tissue has been abraded or removed for repigmentation. The substrate can be fixed in place over the treatment area, e.g., using tape or the like. The substrate can be removed after sufficient time has elapsed to allow attachment and growth of the micrografts in the treatment area, e.g., several days to a few weeks With the exemplary steps described above, systems in accordance with the present teachings can be used to prepare any type of skin graft, such as an epidermal skin graft, a split thickness graft, or a full thickness graft. However, the device of the invention is particularly well suited for preparing skin grafts including only or substantially only the epidermal layer of skin. The device of the invention can be used for autografts, allografts, or xenografts for the repair of numerous different types of skin damage. For example, harvested grafts may be used to treat burns (e.g., both thermal and chemical burns), blistering, dermatological conditions (e.g., epidermolysis bullosa or pyoderma gangrenosum), radiation therapy ulcers, diabetic ulcers, ischemic ulcers, trophic ulcers, trauma, or depigmentation (e.g., vitiligo).

References and citations to other documents, such as patents, patent applications, patent publications, journals, books, papers, web contents, have been made throughout this disclosure. All such documents are hereby incorporated herein by reference in their entirety for all purposes.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A device for obtaining a skin graft, the device comprising:
    a cutting body configured to be disposable on a patient's skin;
    a head configured to be coupled to the cutting body, the head comprising a sealing surface configured to engage with a mating surface on the cutting body such that when the head is engaged with the cutting body on a patient's skin, a sealed chamber is formed over a target region of the patient's skin;
    a fluid delivery conduit connected to the sealed chamber and configured to deliver, into the sealed chamber, a hypotonic fluid for assimilation into the target region of the patient's skin exposed to the sealed chamber;
    a fluid heater configured to warm the hypotonic fluid to a predetermined temperature;
    a negative pressure conduit connected to the sealed chamber and configured to apply a negative pressure within the sealed chamber to raise at least one skin blister within the sealed chamber; and
    a cutter plate within the cutting body and configured to cleave the blister after formation.

2. The device of claim 1, further comprising at least one window formed on a side surface of the head, wherein the at least one window is configured to allow for observation of the at least one skin blister being raised in the chamber.

3. The device of claim 2, wherein at least a portion of said at least one window further comprises a magnification lens.

4. The device of claim 1, wherein the head further comprises at least one light source configured to illuminate the at least one skin blister as the blister is being raised.

5. The device of claim 4, wherein the light source is a light emitting diode (LED).

6. The device of claim 1, wherein the head further comprises at least one temperature measuring element configured to measure temperature of the patient's skin or temperature of the sealed chamber.

7. The device according to claim 6, wherein the temperature measuring element further comprises at least one thermistor.

8. The device according to claim 1, wherein the fluid heater comprises a resistive electrical heating element.

9. The device of claim 1, wherein the a fluid delivery conduit is configured to remove, from the sealed chamber, any hypotonic fluid not assimilated into the target region of the patient's skin exposed to the sealed chamber.

10. A device for obtaining a skin graft, the device comprising:
    a reservoir configured to store a fluid;
    a head having a fluid delivery conduit configured to receive the fluid from the reservoir;
    a fluid heater configured to warm the fluid to a predetermined temperature; and
    a harvester configured for placement on a target region of a patient's skin, the harvester being configured to form a sealing engagement with the head so as to form a chamber over the target region, said head further being configured to receive, through the conduit, the fluid such that the chamber is filled with the fluid and assimilated into the target region causing swelling of the patient's skin at the target region, the head further being configured to provide a negative pressure to the chamber, the harvester further comprising:
        at least one alignment plate having a plurality of holes through which skin blisters from one or more swollen portions of the target region of the patient's skin are raised in response to the negative pressure; and
        a cutting plate having at least one cutting surface for cleaving the skin blisters.

11. The device of claim 10, wherein said at least one alignment plate comprises a top alignment plate and a bottom alignment plate and wherein the cutting plate is disposed therebetween.

12. The device of claim 11, further comprising an actuator for moving the cutting plate from a first position to a second position.

13. The device of claim 12, wherein the actuator is configured to at least partially retract the cutting plate.

14. The device of claim 10, wherein the at least one cutting surface is associated with one of the plurality of holes of the at least one alignment plate.

15. A system for raising and cutting a skin blister, the system comprising:
    a harvester configured to be placed on a target region of a patient's skin, the harvester being configured to define a sealed chamber over the target region, the harvester comprising:
        a reservoir containing a fluid to be infused into the target region;
        a conduit configured to fluidly couple the reservoir to the sealed chamber and the target region, the conduit being configured to deliver the fluid to the target region thereby causing infusion of the fluid into the target region;
a fluid heater configured to warm the fluid to a predetermined temperature;
at least one alignment plate having a plurality of holes through which skin blisters, from the fluid infused target region, can be raised in the presence of negative pressure; and
a cutting plate having at least one cutting surface for cleaving the skin blisters.

16. The system of claim 15, wherein the harvester further comprises a coupler configured to be coupled to the fluid conduit.

17. The system of claim 15, further comprising a reduced pressure source and a fluid flow pathway between said sealed chamber and the reduced pressure source, wherein the reduced pressure source is configured to generate negative pressure in said chamber.

18. The system of claim 15, wherein the fluid is selected from the group comprising purified water, deionized water, water having an electrical conductivity less than 11 microsiemens/cm, and fluid having a lower osmotic pressure than interstitial fluid in the skin at the donor site.

19. The system of claim 15, further comprising a pump configured to deliver the fluid from the reservoir to the chamber through the conduit.

20. The system of claim 19, wherein the pump comprises a reversible pump configured to remove the fluid from the chamber following a dwell time.

21. The system of claim 20, wherein the reversible pump is configured to deliver the fluid removed from the chamber to a waste reservoir.

22. The system of claim 20, wherein the conduit comprises a valve, the valve being configured to divert flow through the conduit to a waste reservoir.

23. The system of claim 19, further comprising a controller for controlling operation of the pump.

24. The system of claim 23, wherein the controller is configured to control the pump so as to provide a predetermined dwell time of the fluid within the chamber.

25. The system of claim 23, further comprising a valve, wherein the controller is configured to switch the valve so as to divert fluid flowing through the conduit to a waste reservoir when the pump is operating in a reverse mode.

26. A system for raising and cutting a skin blister, the system comprising:
a harvester configured for placement on a target region of a patient's skin, the harvester defining a sealed chamber in fluid communication with the target region when the harvester forms a sealing engagement with the patient's skin, the harvester further comprising:
at least one alignment plate having a plurality of holes through which skin blisters can be raised in the presence of negative pressure; and
a cutting plate having at least one cutting surface for cleaving skin blisters after they are formed within the chamber;
a reservoir containing a fluid to be infused into the patient's skin;
a conduit fluidly coupling the reservoir to the chamber;
a pump for delivering the fluid from the reservoir to the chamber through the conduit, the system further comprising a second pump for removing fluid from the chamber; and
a fluid heater configured to warm the fluid to a predetermined temperature.

27. The system of claim 26, wherein the second pump is configured to operate at a higher volumetric flow rate relative to the pump for delivering the fluid from the reservoir to the chamber.

28. A system for raising and cutting a skin blister, the system comprising:
a harvester configured for placement on a target region of a patient's skin, the harvester defining a sealed chamber in fluid communication with the target region when the harvester forms a sealing engagement with the patient's skin, the harvester further comprising:
at least one alignment plate having a plurality of holes through which skin blisters can be raised in the presence of negative pressure; and
a cutting plate having at least one cutting surface for cleaving skin blisters after they are formed within the chamber;
a reservoir containing a fluid to be infused into the patient's skin;
a conduit fluidly coupling the reservoir to the chamber; and
a pump for delivering the fluid from the reservoir to the chamber through the conduit, the system further comprising a fluid heater associated with the reservoir for warming the fluid to be infused.

29. A system for raising and cutting a skin blister, the system comprising:
a harvester configured for placement on a target region of a patient's skin, the harvester defining a sealed chamber in fluid communication with the target region when the harvester forms a sealing engagement with the patient's skin, the harvester further comprising:
at least one alignment plate having a plurality of holes through which skin blisters can be raised in the presence of negative pressure; and
a cutting plate having at least one cutting surface for cleaving skin blisters after they are formed within the chamber;
a reservoir containing a fluid to be infused into the patient's skin;
a conduit fluidly coupling the reservoir to the chamber; and
a pump for delivering the fluid from the reservoir to the chamber through the conduit,
a controller for controlling operation of the pump, the system further comprising a fluid heater, wherein the controller is configured to activate the fluid heater so as to warm the fluid to a predetermined temperature.

* * * * *